United States Patent [19]

Polyak

[11] Patent Number: 5,468,213
[45] Date of Patent: Nov. 21, 1995

[54] MECHANICAL PENILE PROSTHESIS

[75] Inventor: Mark Polyak, Minnetonka, Minn.

[73] Assignee: American Medical Systems, Inc., Minnetonka, Minn.

[21] Appl. No.: 310,918

[22] Filed: Sep. 22, 1994

[51] Int. Cl.⁶ ..................................... A61F 2/26
[52] U.S. Cl. ............................................. 600/40
[58] Field of Search ................... 600/38–41; 623/11–12

[56] References Cited

U.S. PATENT DOCUMENTS

| | | |
|---|---|---|
| 4,151,840 | 5/1979 | Barrington . |
| 4,151,841 | 5/1979 | Barrington . |
| 4,187,839 | 2/1980 | Nuwayser et al. ............ 600/40 |
| 4,392,562 | 7/1983 | Burton et al. ............... 600/40 |
| 4,517,967 | 5/1985 | Timm et al. . |
| 4,522,198 | 6/1985 | Timm et al. . |
| 4,541,420 | 9/1985 | Timm et al. . |
| 4,545,081 | 10/1985 | Nestor et al. . |
| 4,619,251 | 10/1986 | Helms et al. . |
| 4,665,902 | 5/1987 | Goff et al. . |
| 4,693,719 | 9/1987 | Franko . |
| 4,790,298 | 12/1988 | Trick . |
| 4,881,531 | 11/1989 | Timm et al. . |
| 5,050,592 | 9/1991 | Olmedo ...................... 600/40 |

FOREIGN PATENT DOCUMENTS

| | | |
|---|---|---|
| 2740263 | 3/1979 | Germany .................... 600/40 |
| 2151484 | 7/1985 | United Kingdom .......... 600/40 |

Primary Examiner—Angela D. Sykes
Assistant Examiner—J. Lacyk
Attorney, Agent, or Firm—Peter C. Richardson; Lawrence C. Akers; Mark Dryer

[57] ABSTRACT

A mechanical penile prosthesis which comprises an elongated, tubular, prestretched, elastic outer sheath having a distal tip, a proximal tip and an intermediate portion defining a hollow tubular chamber having positioned therein a central core anchored at each of its ends to a tip, and an articulated member positioned about the flexible core, which articulated member comprises a plurality of alternating rings and discs, each of the rings being defined by a toroid having a curved surface, a substantially circular cross-section and an outer circumference, each of the discs being defined by a toroid having a flattened upper surface and a flattened lower surface, each surface having a peripheral portion which has a tapered or convex profile which contacts the curved surface of the adjacent rings.

6 Claims, 1 Drawing Sheet

MECHANICAL PENILE PROSTHESIS

FIELD OF THE INVENTION

This invention relates to a mechanical penile prosthesis having an articulated structure which provides improved positionability over prior art prostheses.

BACKGROUND OF THE INVENTION

Impotence or inability to achieve penile erection is quite prevalent and many solutions have been proposed and are available in the art to cure or compensate for the condition. In particular, various types of penile prostheses are commercially available.

The majority of penile prostheses fall into two types. These two types are the inflatable, implantable prosthesis and the simple implantable inherently stiff or substantially rigid prosthesis. The inflatable prosthesis is normally implanted in pairs within the corpora cavernose and connected to hydraulic pumping means, also implanted within the patient's body, which means enable the prosthesis to be inflated for erection and deflated for flaccidity. The simple or non-inflatable prosthesis is also generally implanted in pairs in the corpora cavernose and, in view of its inherent stiffness, provides a generally constant erection. Hence, it is desirable to provide positionability so that the erection may be at least partially concealed by the patient. Positionability is generally achieved by making the simple prosthesis bendable, and the prosthesis provided by the present invention is of this simple type, herein designated as a mechanical prosthesis.

Some of the mechanical prostheses of the prior art are based upon a rigid but malleable longitudinal core member and these are generally designated as malleable prostheses. Another type of mechanical prosthesis achieves rigidity and positionability through an articulated member and the present invention is concerned with a mechanical prosthesis of this latter type.

U.S. Pat. Nos. 4,151,841 and 4,187,839 disclose implantable penile prostheses having a flexible central longitudinal member.

U.S. Pat. No. 4,665,902 discloses a flexible penile prosthesis having an intermediate tubular section containing a flexible zone. The flexible zone is formed by a plurality of circumferential grooves having sides of unequal length.

U.S. Pat. No. 4,693,719 discloses a penile prosthesis which comprises two or more cylindrical segments which lock into an axially aligned position through the action of a spring plunger.

U.S. Pat. No. 4,790,298 discloses a penile prosthesis having an array of individually pivotable segments which can be rendered into a rigid unit by engagement with interfering members.

U.S. Pat. Nos. 4,151,840, 4,517,967, 4,522,198, 4,541,420, 4,545,081, 4,619,251 and 4,881,531 disclose prostheses utilizing various forms of segmented or articulated structures.

It has now been found that an improved mechanical penile prosthesis of the type having an articulated structure with improved positionability, improved performance and low cost is provided as hereinafter described.

SUMMARY OF THE INVENTION

In accordance with the present invention there is provided a mechanical penile prosthesis for implantation in a corpus cavernosum of a patient, which comprises an elongated tubular outer sheath made from a pre-stretched elastic material and having a distal portion, a proximal portion and an intermediate portion, the distal portion defining a substantially rigid tip, the proximal portion defining a substantially rigid tip, each of said tips terminating in a rounded end, and the intermediate portion defining a hollow tubular chamber having a longitudinal axis, an inner surface and a substantially circular cross-section, a central core having a distal end and a proximal end positioned along said longitudinal axis and anchored at each of said distal and proximal ends to each of said tips, and an articulated member positioned within the chamber about said central core, which articulated member comprises a plurality of alternating rings and discs, each of said rings being defined by a toroid having a curved surface, a substantially circular cross-section and an outer circumference, each of said discs being defined by a toroid having a flattened upper surface and a flattened lower surface, each of said upper and lower surfaces having a peripheral portion with an outer circumference, wherein each peripheral portion has a tapered or convex profile such that the tapered profile is tangential to or the convex profile is complimentary to the curved surface of the ring adjacent to each disc.

The central core is preferably a flexible coil or a pretensioned cable and the central core together with the pre-stretched outer sheath provides a compression force along the articulated portion of the prosthesis which results in a frictional contact between the rings and the discs which support the penis in an erectile condition.

When a bending force is applied to the penis the rings are displaced with respect to the discs so that the articulated portion of the prosthesis acts like a hinge and provides positional stability maintaining the penis in a flaccid condition.

DETAILED DESCRIPTION OF THE INVENTION

The preferred embodiment of a prosthesis according to the invention comprises, in combination, an elongated, prestretched, tubular outer sheath having a substantially rigid tip at each end and, accommodated within a hollow intermediate portion, a central core and an articulated member comprising a plurality of mating rings and discs.

The outer sheath, which also envelopes the tips is preferably made from a biocompatible, elastomeric material which has been prestretched whereby it contributes a compression force along the articulated portion of the prosthesis.

Each of the substantially rigid tips is made from a biocompatible solid material, preferably a solid plastic.

The central core is anchored at its proximal end and distal end to the proximal tip and distal tip, respectively. The core may be a flexible spring coil or a pretensioned flexible cable. The central core also contributes a compression force along the articulated portion of the prosthesis and thus acts in combination with the prestretched outer sheath.

The compression force provided by the stretched outer sheath and pretensioned central core produces contact friction between the rings and discs sufficient to support the penis in the erectile condition when the prosthesis as a whole, including the intermediate articulated portion, is in a straight configuration along the longitudinal axis. When the prosthesis is manually bent into the flaccid position, the articulated portion adopts a hinge-like configuration wherein the rings move relative to the discs. Thus, when the outer circumference of each ring has a diameter greater than the diameter of the outer circumference of each disc the rings are pushed down below the edges of the discs. Alternatively, when the stated diameters are the same or the stated diameter of each ring is less than the stated diameter of each disc the relative movement may produce a less pronounced displacement but the overall effect will be the same. This relative movement enables the prosthesis to provide positional stability when in the bent hinge-like configuration, thus maintaining the penis in a flaccid condition. When a straightening force is applied to the articulated portion in the hinged condition, the rings are pushed up between the discs so that the prosthesis is straightened and the penis is brought to the erect position.

A particular advantage of the mechanical prosthesis according to the invention is that the operational parts are comparatively simple in structure which facilitates manufacture and keeps the cost low compared to the more elaborate articulated devices of the prior art.

BRIEF DESCRIPTION OF THE DRAWINGS

The invention will be more particularly described with reference to a preferred embodiment as illustrated in the accompanying drawings in which.

Figure 1:
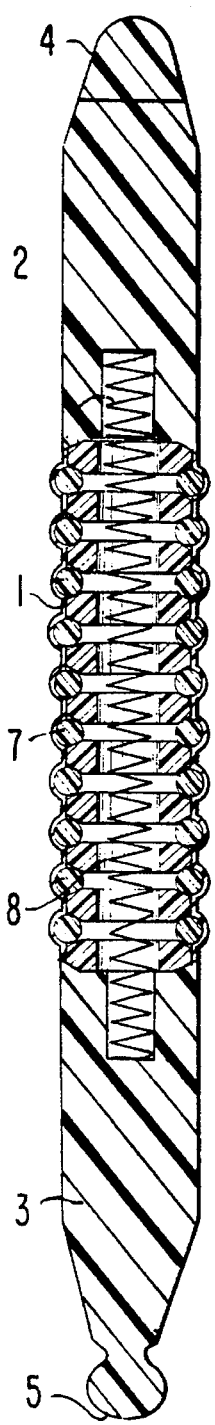
FIG. 1 is a side elevation, partly in section, of a prosthesis in the erectile condition.

The mechanical prosthesis illustrated in FIG. 1 of the accompanying drawings comprises a pre-stretched flexible elastic outer sheath 1 which envelopes and is attached to a distal or front tip 2 and a proximal or rear tip 3. The distal tip terminates in a rounded end 4 which facilitates implantation of the prosthesis in a corpus cavernosum and contributes to the comfort of the patient and the simulation of a naturally-occurring erection. The proximal tip also terminates in a rounded end 5 which, in the preferred embodiment, has a knob-like configuration which allows the tip to receive a snap-on extension, if desired. Alternatively, the proximal tip may have a rounded end (not shown) having a similar configuration to the rounded end of the distal tip. It is to be understood that the distal and proximal appellations are used herein for convenience and for the purpose of implantation the prosthesis may be considered to be reversible.

The intermediate portion of the outer sheath defines a hollow tubular chamber having a longitudinal axis and a substantially circular cross-section. A central core is positioned along the longitudinal axis of the intermediate portion and is anchored at its forward end and rear end to the distal tip and proximal tip, respectively. In the embodiment illustrated in the drawings, the central core is a flexible coil spring 6. Alternatively, the flexible core may be a pretensioned cable or any other flexible element which is capable of contributing a compression force to the articulated portion of the prosthesis.

Figure 2:
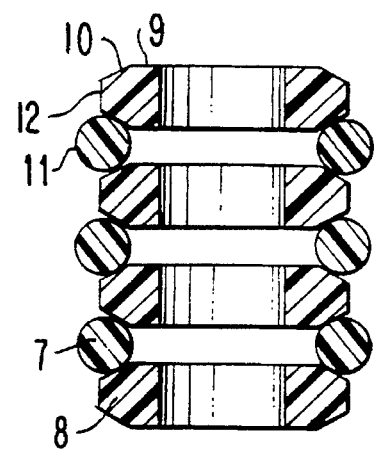
FIG. 2 is an enlarged cross-sectional view of part of the articulated portion of the prosthesis of FIG. 1.
Figure 3:
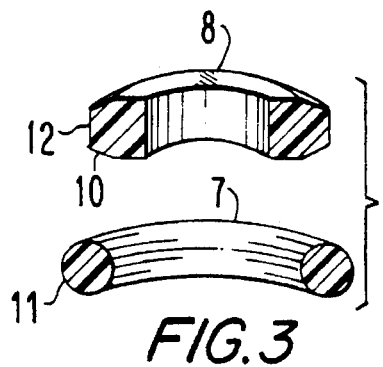
FIG. 3 is an exploded view, partly perspective and partly cross-sectional, of an adjacent ring and disc.
Figure 4:
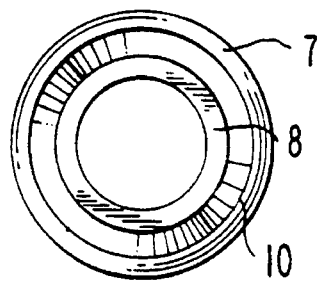
FIG. 4 is a plan view of a single ring and disc.
Figure 6:
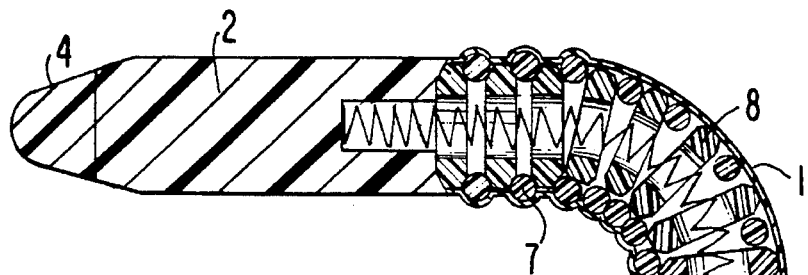
FIG. 6 is an enlarged cross-section through a bent portion of the prosthesis of FIG. 5.
Figure 6:
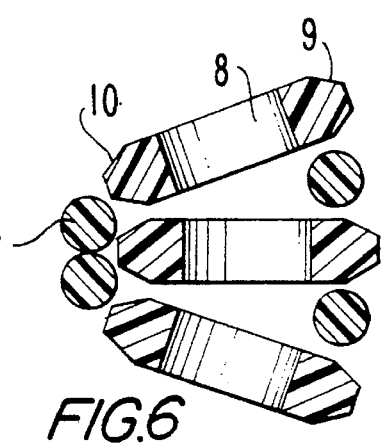
Figure 5:
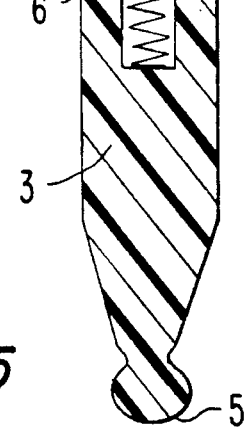
FIG. 5 is a side elevation, partly in section, of a prosthesis in the flaccid condition.

An articulated member is positioned in the intermediate portion about the flexible core and this articulated member comprises a plurality of alternating rings 7 and discs 8. Each of the rings is defined by a toroid of substantially circular cross-section, as illustrated more clearly in the enlarged view of FIG. 2. The flexible core is not shown in either FIG. 2 or FIG. 6. In the illustrated preferred embodiment, the outer circumference of each ring is in contact with the inner surface of the stretched outer sheath. The outer sheath is not shown in FIG. 2.

Each of the discs is defined by a toroid having a flattened upper surface 9 and a flattened lower surface, each surface having a peripheral portion with a tapered profile 10 which is tangential to the curved surface of the adjacent rings. In the illustrated preferred embodiment, the diameter of the outer circumference 11 of each ring is greater than the diameter of the outer circumference 12 of each disc. Instead of a substantially straight tapered profile, the peripheral portion of each disc may have a surface with a convex profile which is complimentary to the curved surface of the adjacent rings. Whether the relevant mating surface of the disc is tapered or convex, the contact between each disc and ring should provide sufficient friction when the articulated member is subjected to a compression force as herein described to maintain the prosthesis in the erectile or flaccid condition, as the case may be.

Preferably, each ring is made from a solid plastic and each disc is made from a solid plastic, which may be the same as or different from the plastic of the ring, provided that there is sufficient friction between the surface of each ring and the mating surface of each adjacent disc to avoid slippage between the surfaces without the application of a manually exerted force. Alternatively, either or both of the rings and discs may be made from a solid material, such as a metal, provided the overall weight is not too excessive and the aforesaid friction requirement is satisfied.

The mating of the contact surfaces of the rings and discs in conjunction with the compression force exercised by the stretched outer sheath and pre-tensioned central core provides sufficient friction to retain the prosthesis in a substantially rigid erectile position. When a manual bending force is applied to the articulated portion the rings slide relative to the discs (see FIG. 6) to provide a bend which maintains the penis in a flaccid position. Until a counter-force is applied to straighten or bend the prosthesis, the penis remains in the flaccid or erect position, as the case may be.

I claim:

1. A mechanical penile prosthesis for implantation in a corpus cavernosum of a patient, which comprises an elongated tubular outer sheath made from a prestretched elastic material and having a distal portion, a proximal portion and an intermediate portion, the distal portion defining a substantially rigid tip, the proximal portion defining a substantially rigid tip, each of said tips terminating in a rounded end, and the intermediate portion defining a hollow tubular chamber having a longitudinal axis, an inner surface and a substantially circular cross-section, a central core having a distal end and a proximal end positioned along said longitudinal axis and anchored at each of said distal and proximal ends to each of said tips, and an articulated member positioned within the chamber about said central core, which articulated member comprises a plurality of alternating rings and discs, each of said rings being defined by a toroid having a curved surface, a substantially circular cross-section and an outer circumference, each of said discs being defined by a toroid having a flattened upper surface and a flattened lower surface, each a said upper and lower surfaces having a peripheral portion with an outer circumference, wherein each peripheral portion has a tapered or convex profile, such that the tapered profile is tangential to or the convex profile is complimentary to the curved surface of the rings adjacent to lock disc.

2. A prosthesis according to claim 1, in which the central core is a flexible spring coil.

3. A prosthesis according to claim 1, in which the central core is a pretensioned flexible cable.

4. A prosthesis according to claim 1, in which the peripheral portion of each disc has a tapered profile tangential to the curved surface of the rings adjacent to each disc and the diameter of the outer circumference of each ring is greater than the diameter of the outer circumference of each disc.

5. A prosthesis according to claim 1, in which the outer sheath is made from a biocompatible elastomeric material and each of the tips is made from a biocompatible solid plastic.

6. A prosthesis according to claim 1, in which each ring is made from a solid plastic and each disc is made from a solid plastic, provided that there is sufficient friction between the curved surface of each ring and the upper and lower surface of each adjacent disc to avoid slippage between the surfaces without the application of a manually exerted force.

* * * * *